(12) United States Patent
Maestro et al.

(10) Patent No.: US 8,142,825 B2
(45) Date of Patent: Mar. 27, 2012

(54) COSMETIC USE OF AN ACTIVE AGENT CAPABLE OF STIMULATING TENSIN 1 EXPRESSION

(75) Inventors: Yannick Maestro, Martigues (FR); Gaëlle Saintigny, Paris (FR); François Xavier Bernard, Saint-Maurice la Clouère (FR)

(73) Assignee: Chanel Parfums Beaute, Neuilly-sur-Seine (FR)

( * ) Notice: Subject to any disclaimer, the term of this patent is extended or adjusted under 35 U.S.C. 154(b) by 0 days.

(21) Appl. No.: 13/157,574

(22) Filed: Jun. 10, 2011

(65) Prior Publication Data

US 2011/0281274 A1 Nov. 17, 2011

Related U.S. Application Data

(62) Division of application No. 12/128,891, filed on May 29, 2008, now abandoned.

(60) Provisional application No. 60/941,730, filed on Jun. 4, 2007.

(30) Foreign Application Priority Data

May 29, 2007 (FR) ...................................... 07 03790

(51) Int. Cl.
*A61K 36/00* (2006.01)
(52) U.S. Cl. ........................................................ 424/725
(58) Field of Classification Search .................. None
See application file for complete search history.

(56) References Cited

FOREIGN PATENT DOCUMENTS

| FR | 2 435 521 A1 | 4/1980 |
|---|---|---|
| JP | 2002053478 | 2/2002 |
| JP | 2006232740 | 9/2006 |
| WO | 2005053718 | 6/2005 |

OTHER PUBLICATIONS

Karmous T. et al: "Non-alcoholic perfumes", Journal of Essential Oil-Bearing Plants, vol. 8, No. 1, 2005, pp. 71-81, XP009111658.
Merle A. et al.: "The Composition of Manila Elemi Oil", Flavour and Fragrance Journal, vol. 8, No. 1, 1993, pp. 35-37, XP002513530.
Halsall, T. G. et al: "The chemistry of triterpenes and related compounds. Part XXI", Journal of the Chemical Society, 1953, pp. 4139-4148, XP009111733.
International Search Report, dated Feb. 25, 2009, in PCT/EP2008/056609.
"Probotix anti-aging serum by bioelements", Product Information [Online], www.dermstore.com/product_probotix+Anti-Aging+Serum_8130.htm, May 1, 2006, XP002464031.
"Bioelements launches new probotix anti-aging serum", Bioelements Press Room [Online], www.bioelements.com/jsp/press_release.jsp?id=401, May 1, 2006, XP002464032.
"Collagen production promoter for use in skin cosmetics as antiaging agent, comprises essential oil obtained from steam distillation of plants e.g. Sambucus nigra, Canarium luzonicum and Thymus", Derwent Publications Ltd., Sep. 7, 2006, XP002464033.
"Platelet aggregation inhibitor in skin external preparation, for preventing and improving dermatological disorders such as contact dermatitis, comprises extract of Canarium plant", Derwent Publications Ltd., Feb. 19, 2002, XP002464034.
Dr. Frederick Brandt, "New lineless anti-glycation serum", TL Communications [Online], www.drbrandtskincare.com/press-release.php?rk=29, Jan. 29, 2007, p. 646, XP002464905.
Lineless anti-glycation serum-full ingredients list [Online], www.drbrabdtskincare.com/full-ingredients.php?pk=109, Jan. 29, 2007, XP002464906.
Iwaki, Haruhi et al., Jul. 9, 2006, Japan, JP 2006-232750 A, Translation.
"Peptides", Internet Archive Date: Jun. 1, 2007 [retrieved from the internet on May 30, 2010]. Retrieved from: <http://web.archive.org/web/20070106021700/http://www.wrinklereview.com/wrinkle-reducer/peptides.html>.

*Primary Examiner* — Amy L Clark
(74) *Attorney, Agent, or Firm* — Young & Thompson

(57) ABSTRACT

A cosmetic skincare process intended to prevent and/or treat at least one cutaneous sign of aging, includes the topical application to the skin of a composition containing at least one active agent capable of stimulating tensin 1 expression. The cosmetic use of an active agent capable of stimulating tensin 1 expression, for preventing and/or treating at least one cutaneous sign of aging, an extract of elemi or of *Canarium indicum* L. or of *Canarium luzonicum* or of *Canarium commune* and a cosmetic composition containing the extract are also disclosed.

4 Claims, No Drawings

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Thr Thr Lys Ser
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Glu Pro Arg
1

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 3
ccgaggcagg auaggaguut t                                           21
```

COSMETIC USE OF AN ACTIVE AGENT CAPABLE OF STIMULATING TENSIN 1 EXPRESSION

The present invention relates to a cosmetic skincare process intended to prevent and/or treat at least one cutaneous sign of aging, comprising the topical application to the skin of a composition containing at least one active agent capable of stimulating tensin 1 expression.

Skin aging is defined by the collection of impairments of the cutaneous covering, resulting from the accumulation over the years of progressive modifications of its various constituents and the disorganization of the existing structures, in particular in the dermis, which constitutes the support tissue for the skin.

A decrease in transmembrane interactions between the components of the extracellular matrix, or ECM (collagens, elastin, glycosaminoglycans, and in particular fibronectin), and the intracellular cytoskeleton of the fibroblasts, which consists of actin filaments, is thus observed in the dermis. These interactions take place at the level of focal adhesions, which are protein complexes located on the plasma membrane of the fibroblasts. These complexes ensure the transmission of bidirectional signals between the intracellular and extracellular compartments. They play an essential role in stabilizing the shape of the cells and the nucleus; in maintaining the organization of the ECM; at the molecular level, in the equilibrium of tensegrity forces and on the biochemical function of the cell (D. Ingber, *Pour la science [For science]*, 1998; Zamir E. et al., *J. Cell Sci.,* 2001). These complexes mainly comprise an $\alpha5\beta1$ intramembrane integrin, which is the receptor specific for fibronectin in the ECM and is directly linked to intracellular proteins. Reduction of the abovementioned interactions leads to molecular disorganization at the adhesion sites, and a decrease in the proliferative capacities of fibroblasts, in their metabolic activity (synthesis of ECM components) and in their migratory capacity (Sottile et al., *Mol. Biol. Cell.,* 2002; Katz et al., *Mol Bio Cell,* 2000). These dysfunctions are responsible for modifications of the biomechanical properties of the skin, and in particular for the slackening of the skin, which is one of the main functional signs of skin aging.

In order to combat slackening of the skin, various cosmetic ingredients for stimulating fibroblast proliferation, such as soybean proteins, or for increasing the synthesis of collagen, elastin and/or glycosaminoglycans, such as ascorbic acid and its derivatives, or else for relaxing the facial muscles responsible for wrinkles and expression lines through the injection of botulin intoxin, have been proposed in the art.

Despite their advantage, these solutions are not entirely satisfactory, since they do not make it possible to treat the problem of slackening of the skin at the source and, consequently, in the long term. In order to maintain the cellular metabolic activity in the dermis and the synthesis of ECM constituents over the long term, it would be desirable to be able to ensure that good rigidity and good organization of the ECM and the interactions between the fibroblasts and their surrounding matrix are maintained.

Tensin 1 is a phosphoprotein which binds to the actin filaments of the cytoskeleton of cells and to the extracellular matrix, at the level of the abovementioned focal adhesions (Chen et al., *PNAS,* 2001; Takahara et al., *J. Histochem. Cytochem.,* 2004) and specifically the intracellular portion of the $\alpha5\beta1$ integrin. In connective tissues and in the dermis, tensin 1 is known to allow integrins to move along the cell membrane and to group together, thus entraining the fibronectin associated with these integrins and modifying the conformation of the fibronectin molecules so as to promote their polymerization (Pankow et al., *J. Cell. Biol.,* 2000), the fibronectin itself playing an essential role in the composition and the stability of the extracellular matrix, and in particular in maintaining collagen I in the form of fibrils. The applicant has demonstrated, for the first time, that tensin 1 is a key protein in the process of the tensioning of the cells of the dermis (fibroblasts) and, in terms of cell activity, for increasing the firmness of the skin and for preventing and/or combating slackening of the skin resulting from the dermal aging process.

The applicant has also demonstrated a decrease in tensin 1 expression during aging, leading to disorganization of the ECM, in particular of fibronectin, and resulting in slackening of the dermis. It has also demonstrated that contraction of the dermis is considerably reduced in the absence of tensin. It therefore appeared to the applicant that the use, in cosmetic compositions, of active agents capable of stimulating tensin 1 could make it possible to combat the slackening of the skin observed during aging.

Finally, the applicant has, to its credit, developed a screening test for selecting biological active agents, and in particular botanical extracts, such as nonoily extracts of plants of the *Canarium* genus, capable of acting topically on tensin 1 in order to stimulate its expression.

Oily extracts of *Canarium* are already known as anti-inflammatory agents for combating wrinkles and loss of skin firmness (WO 2005/053718). However, it has never yet been suggested, to the applicant's knowledge, that nonoily extracts of *Canarium* can provide a cosmetic anti-aging effect, in particular by stimulating tensin 1 expression.

Consequently, a subject of the present invention is a cosmetic skincare process intended to prevent and/or treat at least one cutaneous sign of aging, comprising the topical application to the skin of a composition containing at least one active agent capable of stimulating tensin 1 expression.

A subject of the present invention is also the cosmetic use of an active agent capable of stimulating tensin 1 expression, for preventing and/or treating at least one cutaneous sign of aging.

As a preamble, it is specified that the expression "active agent capable of stimulating tensin 1 expression" is intended to mean a compound or (in particular in the case of a botanical extract) a mixture of compounds capable of stimulating tensin 1 expression compared with a nontreated control, determined in particular using the method described in example 1 hereinafter, i.e. by immunofluorescence on a culture of fibroblasts supplemented with TGFβ. Preferably, the increase in labeling compared with the control is at least 20%.

The active agents that can be used according to the invention are advantageously botanical extracts, i.e. active agents obtained by extraction, using any type of solvent, of any part of a plant, such as the bark, the wood, the rhizomes, the stems, the leaves or the flowers, the exudates such as gum-resins or oleo-gum-resins, for example. Examples of such active agents include extracts (in particular of resin or gum) of elemi, i.e. of *Canarium indicum* L (or *Canarium commune* L) or of *Canarium luzonicum*.

These active agents may, for example, be obtained according to a method comprising:
 a) hydrodistillation of the gum or of the resin of the plant,
 b) elimination of the essential oils,
 c) extraction of the hydrodistillation residues using a polar organic solvent, other than water, having a polarity index of greater than 3.5, such as an alcohol, in particular methanol, ethanol or isopropanol. In all cases, the extraction can be carried out on all or part of the plant under consideration, which can be ground or reduced to pieces in the usual manner. The extraction is generally carried out by immersing or gently stirring the ground material in one or more of the abovementioned solvents at temperatures ranging, for example, from ambient temperature to 100° C., for a period of approximately 30 min to 12 h. The solution is then preferably filtered in order to remove the insoluble substances of the plant. Where appropriate, the solvent, if it is a volatile solvent, for instance ethanol or methanol, is also removed.

This extraction step is commonplace in the field of plant extracts, and those skilled in the art are in a position to adjust the reaction parameters thereof on the basis of their general knowledge.

To the applicant's knowledge, this method nevertheless results in a novel product when it is applied to elemi. A subject of the invention is therefore also an extract of elemi or of *Canarium indicum* L. or of *Canarium luzonicum* or of *Canarium commune*, characterized in that it can be obtained according to the method described above.

A subject of the invention is also a cosmetic composition, characterized in that it comprises, in a cosmetically acceptable medium, at least one such extract.

The active agent capable of stimulating tensin 1 expression can be used in a proportion of from 0.00001 to 5% by weight, preferably in a proportion of from 0.0001 to 0.1% by weight, and more preferably in a proportion of from 0.001 to 0.3% by weight, relative to the total weight of the composition.

The cutaneous signs of aging targeted in the present invention may be signs of chronological (intrinsic) aging or actinic aging (photoaging). The invention is more particularly directed toward preventing and/or treating the cutaneous signs linked to the slowing down of production and/or to the degradation and/or disorganization of collagen, such as the formation of wrinkles and fine lines, loss of firmness of the skin and/or dermal atrophy. The process according to the invention is more particularly intended to prevent and/or combat slackening of the skin.

Preferably, the active agent used according to the invention, or the composition used in the process according to the invention, is applied to human skin, in particular to elderly skin, more particularly to the skin of menopausal women and/or women over the age of 50, or even over the age of 60.

The composition containing this active agent may be applied in the morning and/or the evening, preferably the evening, to the entire face, neck and, optionally, neck and shoulders, or even body.

The composition used according to the invention generally comprises, in addition to the active agent described above, a physiologically acceptable and preferably cosmetically acceptable medium, i.e. a medium which does not cause any sensations of discomfort (redness, tautness, stinging, etc.) which is unacceptable to the user.

This medium generally contains water.

The composition used according to the invention may be in any form that is suitable for topical application to the skin, and in particular in the form of an oil-in-water, water-in-oil or multiple emulsion (W/O/W or O/W/O), which may optionally be microemulsions or nanoemulsions, or in the form of an aqueous dispersion, a solution, an aqueous gel or a powder. It is preferable for this composition to be in the form of an oil-in-water emulsion.

This composition is preferably used as a care or cleansing product for facial and/or bodily skin and it may in particular be in the form of a fluid, a gel or a mousse, packaged for example in a pump-dispenser bottle, an aerosol or a tube, or in form of a cream packaged, for example, in a jar. As a variant, it may be in the form of a makeup product, and in particular a foundation or a loose or compact powder.

It may contain various adjuvants, such as at least one compound chosen from:

oils, which may be chosen in particular from: linear or cyclic, volatile or nonvolatile silicone oils, such as polydimethylsiloxanes (dimethicones), polyalkyl-cyclosiloxanes (cyclomethicones) and polyalkyl-phenylsiloxanes (phenyl dimethicones); synthetic oils such as fluorooils, alkyl benzoates and branched hydrocarbons such as polyisobutylene; plant oils, and in particular soybean oil or jojoba oil; and mineral oils such as liquid paraffin;

waxes, such as ozokerite, polyethylene wax, beeswax or carnauba wax;

silicone elastomers obtained in particular by reaction, in the presence of a catalyst, of a polysiloxane containing at least one reactive group (in particular hydrogen or vinyl) and bearing at least one alkyl group (in particular methyl) or a phenyl group, in a terminal and/or side position, with an organosilicone such as an organohydrogenpolysiloxane;

surfactants, preferably emulsifying surfactants, whether they are nonionic, anionic, cationic or amphoteric, and in particular fatty acid esters of polyols such as fatty acid esters of glycerol, fatty acid esters of sorbitan, fatty acid esters of polyethylene glycol and fatty acid esters of sucrose; fatty alcohol ethers of polyethylene glycol; alkylpolyglucosides; polysiloxane-modified polyethers; betaine and derivatives thereof; polyquaterniums; ethoxylated fatty alcohol sulfate salts; sulfosuccinates; sarcosinates; alkyl and dialkyl phosphates, and salts thereof; and fatty acid soaps;

cosurfactants such as linear fatty alcohols and in particular cetyl alcohol and stearyl alcohol;

thickeners and/or gelling agents, and in particular crosslinked or noncrosslinked, hydrophilic or amphiphilic homopolymers and copolymers, of acrylamidomethylpropane sulfonic acid (AMPS) and/or of acrylamide and/or of acrylic acid and/or of acrylic acid salts or esters; xanthan gum or guar gum; cellulosic derivatives; and silicone gums (dimethiconol);

humectants, such as polyols, including glycerol, propylene glycol and sugars, and glycosaminoglycans such as hyaluronic acid and salts and esters thereof;

organic screening agents, such as dibenzoylmethane derivatives (including butylmethoxydibenzoylmethane), cinammic acid derivatives (including ethylhexyl methoxycinnamate), salicylates, para-aminobenzoic acids, $\beta,\beta'$-diphenyl acrylates, benzophenones, benzylidenecamphor derivatives, phenylbenzimidazoles, triazines, phenylbenzotriazoles and anthranilic derivatives;

inorganic screening agents, based on mineral oxides in the form of coated or uncoated pigments or nanopigments, and in particular based on titanium dioxide or zinc oxide;

dyes;

preservatives;

sequestering agents such as EDTA salts;

fragrances;

and mixtures thereof, without this list being limiting.

The composition may also contain at least one compound with an optical effect such as fillers, pigments, nacres, tensioning agents and mattifying polymers, and mixtures thereof.

The term "fillers" should be understood as meaning colorless or white, mineral or synthetic, lamellar or non-lamellar particles suitable for giving the composition body or rigidity and/or softness, a matt effect and uniformity immediately on application. Fillers that may especially be mentioned include talc, mica, alumina, silica, kaolin, Nylon® powders such as Nylon-12 (Orgasol® sold by the company Atochem), polyethylene powders, polyurethane powders, polystyrene powders, polyester powders, optionally modified starch, silicone resin microbeads such as those sold by the company Toshiba under the name Tospearl®, hydroxyapatite, hollow silica microspheres (Silica Beads® from the company Maprecos) and calcined alumina (Spectral PC-401®).

The term "pigments" should be understood as meaning white or colored, mineral or organic particles that are insoluble in the medium, and which are intended to color and/or opacify the composition. They may be of standard or nanometric size. Among the mineral pigments that may be mentioned are titanium dioxide, zirconium dioxide and cerium dioxide, and also zinc oxide, iron oxide and chromium oxide.

The term "nacres" should be understood as meaning iridescent particles that reflect light. Among the nacres that may be envisaged, mention may be made of natural mother-of-pearl, mica coated with titanium oxide, with iron oxide, with natural pigment or with bismuth oxychloride, and also colored titanium mica.

The mass concentration in the aqueous phase of these fillers and/or pigments and/or nacres is generally from 0.1% to 20% and preferably from 0.2% to 7% by weight relative to the total weight of the composition.

The term "tensioning agent" should be understood as meaning a compound suitable for making the skin taut and, by means of this tension effect, making the skin smooth and reducing or even immediately eliminating wrinkles and fine lines therefrom. Tensioning agents that may be mentioned include polymers of natural origin. The term "polymer of natural origin" means polymers of plant origin, vegetable, algae or bacterial sources, and biotechnology synthetized proteins, polymers derived from integuments, egg proteins and latices of natural origin. These polymers are preferably hydrophilic. Polymers of plant origin that may especially be mentioned include proteins and protein hydrolyzates, particularly extracts of cereals, of legumes and of oil-yielding plants, such as extracts of corn, of rye, of wheat, of buckwheat, of sesame, of spelt, of pea, of bean, of lentil, of soybean and of lupin; and more particularly water-soluble proteins derived from almond (*prunus amygdallus dulcis* (sweet almond) seed extract), which are sold by Silab under the name Polylift BG®. The synthetic polymers are generally in the form of a latex or a pseudolatex and may be of polycondensate type or obtained by free-radical polymerization. Mention may be made especially of polyester/polyurethane and polyether/polyurethane dispersions. Preferably, the tensioning agent is a copolymer of PVP/dimethiconyl acrylate and of hydrophilic polyurethane (Aquamere S-2001® from the company Hydromer).

The term "mattifying polymers" means herein any polymer in solution, in dispersion or in the form of particles, which reduces the sheen of the skin and which unifies the complexion. Examples that may be mentioned include silicone elastomers; resin particles; and mixtures thereof. Examples of silicone elastomers that may be mentioned include the products sold under the name KSG® by the company Shin-Etsu, under the name Trefil®, BY29® or EPSX® by the company Dow Corning or under the name Gransil® by the company Grant Industries.

The composition used according to the invention may also comprise active agents other than that which stimulates tensin 1 expression, and in particular at least one active agent chosen from: agents for stimulating the production of growth factors; antiglycation or deglycating agents; agents for increasing collagen synthesis or preventing collagen degradation (anticollagenase agents, in particular matrix metalloproteinase inhibitors); agents for increasing elastin synthesis or preventing elastin degradation (anti-elastase agents); agents for increasing the synthesis of glycosaminoglycans or of proteoglycans or for preventing their degradation (antiproteoglycanase agents); agents for stimulating integrin synthesis by fibroblasts; agents for increasing keratinocyte proliferation or differentiation; agents for increasing fibroblast proliferation; depigmenting or antipigmenting agents; hydration agents; antioxidants, free-radical scavengers or antipollution agents; agents for increasing epidermal lipid synthesis; and mixtures thereof, without this list being limiting.

Examples of such agents are, in particular: extracts of plants, and in particular extracts of *Chondrus crispus*, of *Thermus thermophilus*, of *Pisum sativum*, of *Centella asiatica*, of *Scenedesmus*, of *Moringa pterygosperma*, of witch hazel, of *Castanea sativa*, of *Hibiscus sabdriffa*, of *Polyanthes tuberosa*, of *Argania spinosa*, of *Aloe vera*, of *Narcissus tarzetta*, or of licorice; an essential oil of *Citrus aurantium* (Neroli); an extract of a microalga *Chlorella vulgaris* which is in particular sold by the company CODIF under the trade name Dermochlorella® D/DP; α-hydroxy acids such as glycolic acid, lactic acid and citric acid, and esters thereof; β-hydroxy acids, such as salicylic acid and derivatives thereof; plant protein hydrolysates (in particular soybean or hazelnut hydrolysates); acyl oligopeptides; extracts of yeast, and in particular of *Saccharomyces cerevisiae*; extracts of algae, and in particular of *Laminaires*; vitamins and derivatives thereof, such as retinyl palmitate, ascorbic acid, ascorbyl glucoside, magnesium ascorbyl phosphate or sodium ascorbyl phosphate, ascorbyl palmitate, ascorbyl tetraisopalmitate, ascorbyl sorbate, tocopherol, tocopheryl acetate and tocopheryl sorbate; methacryloyloxyethylphosphorylcholine homopolymers and copolymers; urea; an ether of polyalkylene glycol and glycerin, made for instance from polyethylene glycol, polypropylene glycol and/or polybutylene glycol and preferably from a mixture thereof, such as the product sold by NOF under the trade name Wilbride® S-753; sodium hyaluronate; ceramides and phospholipids; arbutin; kojic acid; ellagic acid; and mixtures thereof.

According to a preferred embodiment, the composition used in the process according to the invention contains at least one active agent for stimulating the synthesis of extracellular macromolecules, and in particular of collagen IV and/or of hyaluronan and/or of fibronectin, such as at least one acyl oligopeptide. The oligopeptide may in particular be chosen from the sequences lysyl-threonyl-threonyl-lysyl-serine (SEQ ID NO: 1), glycyl-histidyl-lysine and glycyl-glutamyl-prolyl-arginine (SEQ ID NO: 2), and mixtures thereof, modified with an alkanoyl group which contains at least 6 and preferably at least 10 carbon atoms, in particular a palmitoyl group. An active agent of this type is in particular sold by the company Sederma under the trade name Matrixyl® 3000.

As a variant or in addition, the composition used according to the invention may comprise at least one antioxidant, which is preferably water-soluble, and which preferably has the property of reducing hydroperoxides, such as the carcinine hydrochloride which is in particular sold by the company Exsymol under the trade name Alistin®.

As a variant or in addition, the composition used according to the invention may comprise at least one agent able to increase the mobility of fibroblasts and keratinocytes and to promote the production of adhesion proteins and/or cytoskeleton proteins of human skin (integrin, actin, vimentin), such as opal powder or hydrated silicon dioxide, which consists of spheres of silica of fairly regular size between 10 to 800 nm, specifically between 10 to 200 μm and which is sold especially by the company Merck under the trade name Opal®.

As a variant or in addition, the composition used according to the invention may comprise at least one agent able to stimulate elafin expression in keratinocytes and to protect the extracellular matrix by preventing the degradation of elastin induced by elastase, such as a *Dilsea carnosa* extract (Dumontiaceae family, red algae), which is sold especially by the company Codif International under the trade name Dilsea Carnosa®.

As a variant or in addition, the composition used according to the invention may comprise at least one agent able to activate the growth of human fibroblasts and the synthesis of collagen from dermal fibroblasts, such as a Nyctanthes Abor-Tristis leaf extract (also called night jasmine or Parijata Flowers), which is sold especially by the company LSN-Cognis under the trade name Noctiliss LS 9803®.

Alternatively or additionally, the composition used according to the invention may comprise at least one agent that activates the microcirculation and/or has anti-edematous properties, such as "acetyl tetrapeptide-5", which allows for the reduction of eye puffs and is marketed by Lipotec under the trade name Eyeseryl®; or such as escin, which is sold by Indena under the trade name Phytosome Escine/β-sitosterol®.

The invention will now be illustrated by the following nonlimiting examples.

EXAMPLES

Example 1

Test for Stimulation of Tensin Expression by Extract of Elemi (*Canarium commune*)

The effect of an extract of elemi (*Canarium commune*) on tensin 1 expression was evaluated.
Protocol:
Preparation of the Extract of Elemi (*Canarium commune*):
This extract is obtained by hydrodistillation of elemi gums, elimination of the essential oil obtained, recovery of the distillation residues (exhausted gums) and ethanolic extraction, filtration and recovery of the filtrate and evaporation of the ethanol, taking up with dipropylene glycol and filtration so as to obtain a pasty liquid extract. The following steps are carried out:
1st Step: Hydrodistillation
 a. Insertion of 150 g of crude elemi gum resin into a conventional hydrodistillation apparatus.
 b. Distillation of the essential oil until exhaustion of the gum resins.
 c. Cooling of the distillation apparatus and filtration of the distillation residues.
 d. Drying of the exhausted elemi gums.
The yield from this step is 25% with respect to essential oil, i.e. 75% with respect to exhausted gum resins.
2nd Step: Ethanolic Extraction
 a. Insertion into a reactor of 100 g of exhausted gum with 500 ml of ethanol at 96.3% (vol/vol).
 b. Stirring of the mixture for 1 h at 60° C.
 c. Cooling of the solution.
 d. Filtration of the solution through Buchner funnel and recovery of the filtrate.
 e. Evaporation of the ethanol with a rotary evaporator.
The yield from this second step is 82%.
3rd Step: Taking Up with Dipropylene Glycol
 a. Insertion into a reactor of 10 g of the ethanolic extract with 10 g of dipropylene glycol and 30 ml of ethanol at 96.3% (volume/volume).
 b. Stirring of the mixture for 30 minutes at 50° C.
 c. Cooling of the solution to ambient temperature.
 d. Filtration.
 e. Evaporation of the ethanol on a rotary evaporator.
 f. Recovery of 20 g of extract in solution in dipropylene glycol. An extract containing 50% by weight of dipropylene glycol is thus obtained.

The extract thus obtained was subsequently diluted to 0.0003% by weight in the culture medium.

Test for Stimulation of Tensin 1 Expression:
Cells (fibroblasts) isolated from skin samples derived from 5 donors, obtained by plastic surgery, were cultured in plastic microplates using DMEM medium supplemented with 2 mM of L-glutamine, 50 IU/ml of penicillin, 50 μg/ml of streptomycin and 10% of fetal calf serum (FCS). The culture medium and the supplements were obtained from Invitrogen. The stimulation of tensin 1 expression was controlled after the addition of TGFβ (R&D Systems) at 10 ng/ml.

The cells were subsequently placed in wells at a rate of 1000 cells per well, on a 96-well plate, and cultured for 72 hours. Fixing/permeabilization was carried out in a phosphate buffer (PBS, Invitrogen) containing 4% of paraformaldehyde (Sigma) and 0.1% of Triton X-100 (Sigma). The saturation, labeling and washing steps were carried out in PBS containing 0.05% of Tween 20 (Sigma), possibly supplemented with 5 g/l of dry skimmed milk (saturation). The monoclonal primary antibody against human tensin 1 (TNS1) comes from BD Transduction Laboratories. The secondary antibodies coupled to the Alexa fluor 488 fluorescent agent came from Invitrogen. The nuclei were stained using a Hoechst dye, bisbenzimide in solution in PBS/Tween (Sigma). The plates were analyzed using an InCell 1000 analyzer (GE Healthcare). A minimum of 5 fixed zones of each well were used for the image analysis and at least 3 wells were used for each of the culture conditions (triplicate). The image analysis was carried out using the Toolbox 1.5 software (GE Healthcare). After calibration of the minimum fluorescence threshold, the fluorescence signal (FS) was expressed as labeled (positive) surface area (in $\mu m^2$) related to the number of cells.

Results:
An average labeled surface area of 87138 (±18188) $\mu m^2$ was measured, i.e. a percentage variation of +48% relative to the nonstimulated control ($p<0.05$).

This assay thus shows that the extract of elemi tested significantly stimulates tensin 1 expression.

Example 2

Immunofluorescence Evaluation of Tensin 1 Expression in Various Skin Samples

In a manner similar to example 1, the expression of tensin 1, of α5 integrin and of fibronectin was compared by immunofluorescence on cultures of fibroblasts from a skin sample originating from breast surgery (normal adult human skin, pool of 5 donors 21 to 51 years old, pool PF2) and used either at the 8th passage (normal fibroblasts), or after artificial aging of the same skin sample using the Hayflic replicative senescence model (aged fibroblasts) (Hayflick, L., *Clin Geriatr Med*, 1985; Hayflick, L. *How and Why We Age*, Ballantine Books, 1994) and from a skin sample from a child (pool of 5 donors 3 to 5 years old) (young fibroblasts). The normal adult fibroblasts are used as a control. The protocol used in this study is identical to that described in example 1. The primary antibodies against human α5 integrin (CD49e) and human fibronectin come from Immunotech and from Sigma, respectively.

The results are given in table 1 below.

TABLE 1

| Protein | Type of human fibroblasts | FS ($\mu m^2$) | Standard deviation | % of control |
|---|---|---|---|---|
| TNS1 | Normal | 0.225 | ±0.032 | 100 |
|  | Aged | 0.153 | ±0.026 | 68 ($p < 0.01$) |
|  | Young | 0.23 | ±0.022 | 101 |
| α5 integrin | Normal | 0.449 | ±0.072 | 100 |
|  | Aged | 0.317 | ±0.016 | 71 ($p < 0.05$) |
|  | Young | 0.459 | ±0.032 | 102 |
| Fibronectin | Normal | 1814 | ±111 | 100 |
|  | Aged | 1367 | ±34 | 75 ($p < 0.01$) |
|  | Young | 1921 | ±125 | 101 |

It is thus observed that the amount of the abovementioned three proteins is reduced by approximately 30% in the aged cells, compared with the normal human skin.

These results thus demonstrate that tensin 1 expression in human skin decreases with age.

Example 3

RT-QPCR Evaluation of Tensin 1 Expression in Various Skin Samples

Protocol:

After culturing, the cells prepared as described in example 1 were washed in order to remove the serum, and the total RNA was extracted with a Tri-Reagent® (Sigma) according to the standard protocol. Samples (triplicates) were collected and treated with DNAse using the DNA-Free® system (Ambion). The qualitative and quantitative analysis of the RNA was carried out using a Bio-Analyzer (Agilent). The reverse transcriptions (RT; Superscipt II® enzyme, Invitrogen) were carried out on 1 µg of DNA-free total RNA and 10 ng of cDNA were finally used for the purpose of the analysis by the real-time polymerase chain reaction (PCR) amplification method (quantitative PCR or QPCR). The QPCR analyses were carried out using the Light Cycler 480 machine with detection using the "SYBR Green I Master®" mix. The following primers were selected from the following GENBANK sequences: G3PDH (NM 002046), TNS1 (NM 022648) and ITGA5 (NM 002205). All the fragments amplified were unique and were sequenced for identity verification. The expression values were related to the expression of the G3PDH housekeeping gene under identical culturing conditions. The results are expressed as percentage of the respective controls.

Results:

The RT-QPCR analysis of TNS1 expression confirmed, after culturing for 48 hours, the results obtained by immunofluorescence in example 2. The mRNAs encoding tensin 1 (TNS1) and α5 integrin (ITGA5) were reduced by approximately 50% for the aged fibroblasts. The increase in culturing time from 48 to 96 hours further decreased the relative amount of TNS1 mRNA in the aged fibroblasts, with the value being 30% of that obtained for the control (normal skin sample). Conversely, the mRNA encoding tensin 1 represented, for the child fibroblasts, 140% of that of the control.

This test thus confirms that tensin and α5 integrin expression decreases with age.

Example 4

Effect of Tensin 1 Inactivation a) Test for Partial Inactivation of TNS1 and Effect on the Expression and Localization of Markers The fibroblasts derived from normal skin samples described in example 2 were transfected with a total of 90 nM of silencing RNA (SiRNA Ambion AM 16708A), complexed with a Lipofectamine LTX (Invitrogen) reagent in an Opti-MEM medium (Invitrogen), according to the supplier's protocol. Three different RNAs that inactivate human TNS1 (ref 50-52) were tested. An irrelevant silencing RNA and the transfection reagent without DNA were used as controls. The silencing RNA ref. 52 (SiRNA ID 139898; sense sequence CCGAGGCAGGAUAGGAGUUtt (SEQ ID NO: 3)) was chosen based on preliminary experiments and used for the subsequent inactivation and functional studies. After transfection, these cells were treated with 10 ng/ml of TGFβ, or were not treated. The analysis of the mRNA (RT-QPCR) and the immunofluorescence analysis were carried out after 48 hours and 72 hours, respectively, as in examples 2 and 3.

The silencing RNA ref. 52 gave the best results, insofar as it reduced TNS1 expression, measured by quantitative analysis of the fluorescence signal derived from the RT-QPCR analysis, by 60%. The inactivation was even greater for the cells stimulated with TGFβ. This level of inactivation was stable for at least 72 hours. It will also be noted that the quantitative levels of expression of α5 integrin and of fibronectin (which also participate in the focal adhesion process) were not affected by the silencing RNA used. On the other hand, the distribution of the α5 integrin and fibronectin fluorescence is altered in the presence of the silencing RNA ref. 52. In fact, in the latter case, the fluorescence no longer appears to be concentrated at the focal adhesion sites. Consequently, the (partial) inactivation of tensin 1 does not change the level of expression of α5 integrin or of fibronectin, but changes the distribution of these markers, which are no longer present at the adhesion sites.

b) Test for Contraction of Collagen Lattices

The lattices were prepared in 6-well plates, $7 \times 10^4$ cells (normal, aged and child cells, as described in example 2) being cultured in a standard medium supplemented with 2.4 mg/well of rat tail collagen I (J Boy Institute), in the presence and absence of 10 ng/ml of TGFβ. The cells transfected with the silencing RNA were used 48 h after transfection in the contraction test. After polymerization for 1 h, the dermal equivalents (DE) were detached manually from their support and kept floating for 8 hours in the culture medium. The medium was changed and a computer image analysis was carried out on days 1, 3, 6 and 8. The surfaces were measured using Lucia 3.0 software (Nikkon).

Preliminary tests aimed at analyzing the contraction capacity of the lattices formed by the various fibroblast populations revealed that the child fibroblasts exhibited the greatest contraction capacity (1000 $mm^2$ to 200 $mm^2$). The contraction was considerably less in the lattices of aged fibroblasts (1000 $mm^2$ to 350 $mm^2$).

In order to evaluate a possible involvement of tensin 1 in the lattice contraction process, lattices were prepared using normal fibroblasts transfected with the silencing RNA ref. 52

(inactivated TNS1). The lattices containing the fibroblasts treated with the transfection mixture were used as controls.

It was clearly observed that the fibroblasts with inactivated TNS1 exhibited a considerable reduction in their ability to contract the collagen lattice (1000 mm$^2$ to 380 mm$^2$) compared with the controls (1000 mm$^2$ to 200 mm$^2$).

This test therefore shows that tensin 1 is involved in the collagen lattice contraction process.

Example 5

Cosmetic Compositions

The following compositions can be prepared in a manner conventional to those skilled in the art. The amounts indicated below are expressed as percentages by weight.

| 5A - SPF 15 Day cream | |
|---|---|
| Tetrasodium EDTA | 0.10% |
| UV-screening agents | 10.49% |
| Cetyl alcohol | 1.00% |
| Glycerol | 5.89% |
| Glycols | 0.68% |
| Aqueous-phase gelling agents | 1.09% |
| Sodium hyaluronate | 0.025% |
| Nonionic emulsifiers | 3.00% |
| Emollients | 16.93% |
| Elemi extract[1] | 0.05% |
| Water-glycol solution of decarboxycarnosine hydrochloride[2] | 1.00% |
| Film-forming polymers | 2.70% |
| Palmitoyl oligopeptide-Palmitoyl tetrapeptide-3[3] | 3.00% |
| Fillers | 1.00% |
| Preserving agents | 0.80% |
| Hydrated silica[4] | 0.20% |
| Fragrance | qs |
| Dyes | qs |
| Water | qsp 100.00% |

[1]Prepared as described in Example 1
[2]Alistin ® from Exsymol
[3]Matrixyl ® 3000 from Sederma
[4]Opal powder from Merck

| 5B - SPF 15 fluid | |
|---|---|
| Tetrasodium EDTA | 0.10% |
| UV-screening agents | 9.49% |
| Cetearyl alcohol | 2.00% |
| Glycerol | 2.50% |
| Glycols | 3.68% |
| Aqueous-phase gelling agents | 4.63% |
| Hydrating agents | 2.53% |
| Nonionic emulsifiers | 1.80% |
| Emollients | 6.60% |
| Elemi extract[1] | 0.05% |
| Water-glycol solution of decarboxycarnosine hydrochloride[2] | 1.00% |
| Film-forming polymers | 0.60% |
| Palmitoyl oligopeptide-Palmitoyl tetrapeptide-3[3] | 3.00% |
| Preserving agents | 0.55% |
| Hydrated silica[4] | 0.20% |
| Fragrance | qs |
| Dyes | qs |
| Water | qsp 100.00% |

[1]Prepared as described in Example 1
[2]Alistin ® from Exsymol
[3]Matrixyl ® 3000 from Sederma
[4]Opal powder from Merck

| 5C - Serum | |
|---|---|
| Tetrasodium EDTA | 0.05% |
| Alcohol | 10.00% |
| Glycerol | 4.65% |
| Glycols | 0.72% |
| Aqueous-phase gelling agents | 1.30% |
| Nonionic emulsifiers | 1.00% |
| Emollients | 9.90% |
| Elemi extract[1] | 1.00% |
| Water-glycol solution of decarboxycarnosine hydrochloride[2] | 1.00% |
| Film-forming polymer | 1.00% |
| Palmitoyl oligopeptide-Palmitoyl tetrapeptide-3[3] | 3.00% |
| Prunus amygdallus dulcis (sweet almond) Seed extract[4] | 2.00% |
| Preserving agents | 0.21% |
| Hydrated silica[5] | 0.20% |
| Dilsea carnosa extract[6] | 2.50% |
| Fragrance | qs |
| Dyes | qs |
| Water | qsp 100.00% |

[1]Prepared as described in Example 1
[2]Alistin ® from Exsymol
[3]Matrixyl ® 3000 from Sederma
[4]Polylift BG ® from Silab
[5]Opal powder ® from Merck
[6]Dilsea Carnosa ® from Codif International

| 5D - Night cream | |
|---|---|
| Tetrasodium EDTA | 0.05% |
| Cetearyl alcohol | 4.80% |
| Glycerol | 9.13% |
| Glycols | 2.68% |
| Aqueous-phase gelling agents | 0.75% |
| Sodium hyaloronate | 0.05% |
| Hydrating agents | 0.50% |
| Nonionic emulsifiers | 1.80% |
| Emollients | 16.45% |
| Elemi extract[1] | 0.05% |
| Water-glycol solution of decarboxycarnosine hydrochloride[2] | 1.00% |
| Palmitoyl oligopeptide-Palmitoyl tetrapeptide-3[3] | 3.00% |
| Nyctanthes Abor-Tristis leaf extract[4] | 5.00% |
| Preserving agents | 0.25% |
| Fillers | 1.96% |
| Fragrance | qs |
| Dyes | qs |
| Water | qsp 100.00% |

[1]Prepared as described in Example 1
[2]Alistin ® from Exsymol
[3]Matrixyl ® 3000 from Sederma
[4]Noctiliss LS 9803 ® from LSN-Cognis

| 5E - Eye cream | |
|---|---|
| Tetrasodium EDTA | 0.10% |
| Cetearyl alcohol | 2.00% |
| Glycerol | 7.89% |
| Glycols | 8.03% |
| Aqueous-phase gelling agents | 0.34% |
| Sodium hyaloronate | 0.05% |
| Nonionic emulsifiers | 1.25% |
| Emollients | 11.25% |
| Elemi extract[1] | 0.05% |
| Water-glycol solution of decarboxycarnosine hydrochloride[2] | 1.00% |
| Palmitoyl oligopeptide-Palmitoyl tetrapeptide-3[3] | 3.00% |
| acetyl tetrapeptide-5[4] | 1.00% |
| Preserving agents | 0.30% |
| Fillers | 0.26% |

5E - Eye cream

| | |
|---|---|
| Fragrance | qs |
| Dyes | qs |
| Water | qsp 100.00% |

(1)Prepared as described in Example 1
(2)Alistin ® from Exsymol
(3)Matrixyl ® 3000 from Sederma
(4)Eyeseryl ® from Indena These compositions can be applied to the face in order to firm the skin.

The invention claimed is:

1. A method for screening an active compound or mixture of compounds capable of treating at least one cutaneous sign of aging comprising:
    treating a culture of fibroblasts supplemented with TGFβ with a compound or a mixture of compounds;
    measuring the ability of said compound or mixture of compounds to stimulate tensin 1 expression in the fibroblasts; and
    determining which compound or compounds are capable of stimulating tensin 1 expression, wherein said compound or mixture of compounds are capable of treating at least one cutaneous sign of aging.

2. The method of claim 1, wherein
    the ability to stimulate tensin 1 expression is measured by immunofluorescence, and
    the tensin 1 expression is indicated as a fluorescence signal expressed in terms of labeled surface area.

3. The method of claim 2, further comprising
    retaining the compound or mixture of compounds providing an increase in labeled surface area of at least 20% compared to the labeled surface area provided by a control.

4. The method of claim 2, further comprising
    retaining the compound or the mixture of compounds providing an increase in labeled surface area of at least 20% over the labeled surface area provided by a culture of fibroblasts supplemented with TGFβ without treatment with the compound or the mixture of compounds.

* * * * *